United States Patent [19]

Mark

[11] Patent Number: 4,552,949

[45] Date of Patent: Nov. 12, 1985

[54] POLYCARBONATE OF SPIRO DIHYDRIC PHENOL

[75] Inventor: Victor Mark, Evansville, Ind.

[73] Assignee: General Electric Company, Mt. Vernon, Ind.

[21] Appl. No.: 544,004

[22] Filed: Oct. 21, 1983

[51] Int. Cl.[4] .............................................. C08G 63/62
[52] U.S. Cl. .................................... 528/201; 525/437; 525/439; 525/444; 525/462; 525/466; 528/190; 528/193; 528/196; 528/204
[58] Field of Search ........................ 528/201, 204, 196

[56] References Cited

U.S. PATENT DOCUMENTS 3,856,526 12/1974 Hamb et al. ............................. 96/48
4,316,980 2/1982 Idel et al. .............................. 528/201

*Primary Examiner*—Harold D. Anderson
*Attorney, Agent, or Firm*—Myron B. Kapustij; Martin B. Barancik

[57] ABSTRACT

Polycarbonates exhibiting improved heat distortion temperatures which are comprised of the polymerized coreaction products of (i) a carbonate precursor, and (ii) at least one particular spiro dihydric phenol. These carbonate polymers are useful in the production of molded articles, sheet glazing materials, and films.

15 Claims, No Drawings

POLYCARBONATE OF SPIRO DIHYDRIC PHENOL

BACKGROUND OF THE INVENTION

Polycarbonates are well known thermoplastic materials which, due to their many advantageous properties, find use as thermoplastic engineering materials in many commercial and industrial applications. The polycarbonates exhibit, for example, excellent properties of toughness, flexibility, impact resistance and high heat distortion temperatures. The polycarbonates and their preparation are disclosed, for example, in U.S. Pat. Nos. 3,028,365; 3,334,154; 3,275,601 and 3,915,926.

There is, however, a need in certain applications, such as those involving a high temperature environment, for polycarbonates exhibiting even higher heat distortion temperatures than those possessed by presently available polycarbonates. It is known to increase the heat distortion temperatures of polycarbonates by adding thereto various polymer systems which exhibit high heat distortion temperatures such as polyarylates, polysulfones, and the like. These resulting blends, however, suffer from certain disadvantages such as being opaque, undergoing phase separation and delamination, and loss of certain unique properties of unblended polycarbonates such as impact strength and the like.

There thus exists a need for polycarbonates exhibiting improved heat distortion temperatures while simultaneously retaining, to a substantial degree, substantially most of the other advantageous properties of conventional polycarbonates. It is, therefore, an object of the instant invention to provide polycarbonates exhibiting improved heat distortion temperatures.

SUMMARY OF THE INVENTION

In accordance with the instant invention there are provided novel polycarbonates exhibiting improved heat distortion temperatures. These polycarbonates are derived from (i) a carbonate precursor, and (ii) at least one particular spiro dihydric phenol.

DESCRIPTION OF THE INVENTION

According to the present invention there are provided polycarbonates exhibiting improved heat distortion temperatures while simultaneously exhibiting, to a substantial degree, substantially most of the other advantageous properties of conventional polycarbonates such as toughness, flexibility, optical clarity, impact strength, and the like.

These novel polycarbonates are derived from, as essential reactants, (i) a carbonate precursor, and (ii) at least one spiro dihydric phenol selected from spiro dihydric phenols represented by the general formula

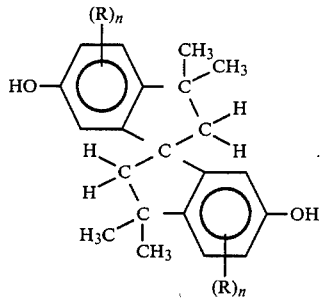

wherein:
R is independently selected from monovalent hydrocarbon radicals and halogen radicals; and
n is independently selected from positive integers having a value of from 0 to 3 inclusive.

The monovalent hydrocarbon radicals represented by R include the alkyl radicals, the cycloalkyl radicals, the aryl radicals, the aralkyl radicals, and the alkaryl radicals.

The alkyl radicals represented by R are preferably those containing from 1 to about 12 carbon atoms. These include the branched alkyl radicals and the straight chain alkyl radicals. Some illustrative non-limiting examples of these alkyl radicals include methyl, ethyl, propyl, isopropyl, butyl, tertiary-butyl, pentyl, neopentyl, and hexyl.

The cycloalkyl radicals represented by R are preferably those containing from 4 to about 7 ring carbon atoms. These include cyclobutyl, cyclopentyl, cyclohexyl, methylcyclohexyl, and cycloheptyl.

The aryl radicals represented by R are preferably those containing from 6 to 12 ring carbon atoms. These include phenyl, biphenyl, and naphthyl.

Preferred aralkyl and alkaryl radicals represented by R are those containing from 7 to about 14 carbon atoms. These include, but are not limited to, benzyl, ethylphenyl, phenylbutyl, phenylpropyl, propylphenyl, and phenylethyl.

The preferred halogen radicals represented by R are chlorine and bromine.

Preferably R is independently selected from chlorine, bromine, and lower alkyl radicals containing from 1 to about 5 carbon atoms.

In the dihydric phenol compound of Formula I when more than one R substituent is present they may be the same or different. The positions of the hydroxyl groups and R on the aromatic nuclear residues may be varied in the ortho or meta positions.

The spiro dihydric phenols of Formula I are compounds that are known in the art and are commercially available or may be readily prepared by known methods. These methods of preparation of the spiro dihydric phenols of Formula I include those described by R. F. Curtis and K. O. Lewis in *Journal of the Chemical Society* (England), 1962, p. 420, and R. F. Curtis in *Journal of the Chemical Society* (England), 1962, p. 417.

These spiro dihydric phenols may be conveniently prepared by (i) reacting two moles of a phenol with one mole of acetone, and (ii) thereafter coreacting 3 moles of the product of (i) under acidic conditions to form the spiro dihydric phenols of Formula I and 4 moles of a phenol. The acids which may be utilized in (ii) can include such acids as anhydrous methane sulfonic acid, anhydrous hydrochloric acid, and the like.

Some illustrative non-limiting examples of the spiro dihydric phenols of Formula I include:

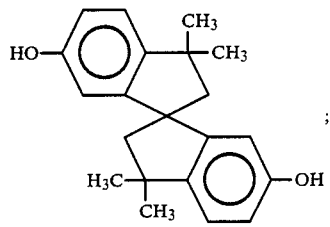
;

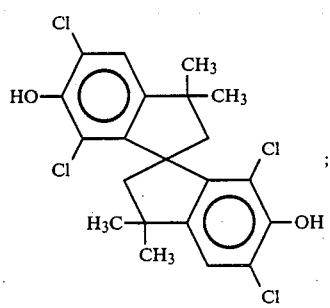
;

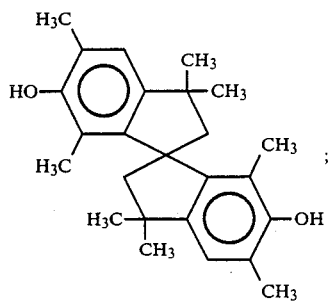
;

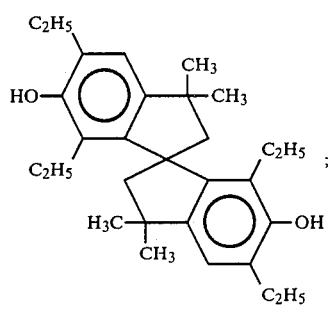
;

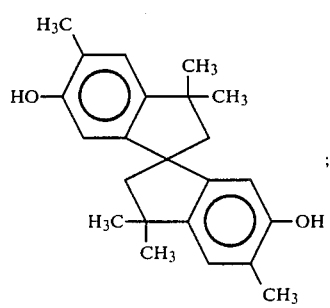
;

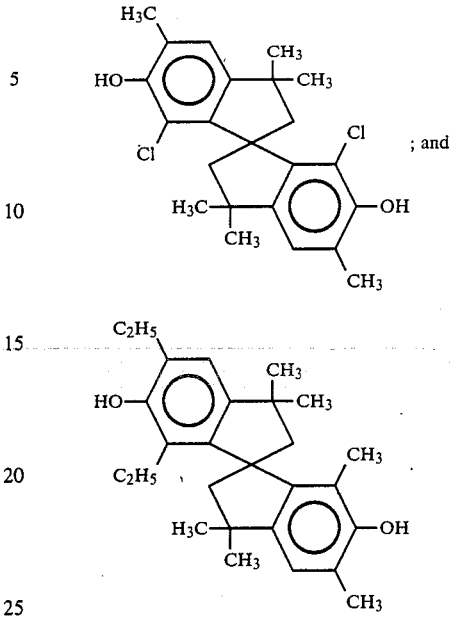
; and

It is, of course, possible to employ mixtures of two or more dihydric phenols of Formula I if a carbonate copolymer rather than a homopolymer is desired.

The carbonate precursor may be a carbonyl halide, a bishaloformate or a diarylcarbonate. The carbonyl halides include carbonyl chloride, carbonyl bromide, and mixtures thereof. The bishaloformates include the bishaloformates of dihydric phenols such as bischloroformates of 2,2-bis(4-hydroxphenyl)propane, 2,2-bis(4-hydroxy-3,5-dichlorophenyl)propane, hydroquinone, and the like, or the bishaloformates of glycols such as the bischloroformates of ethylene glycol, neopentyl glycol, polyethylene glycol, and the like. Typical of the diarylcarbonates which may be employed are diphenyl carbonate; di-(halophenyl)carbonates such as di-(chlorophenyl)carbonate, di-(bromophenyl)carbonate, di-( trichlorophenyl)carbonate, di-(tribromophenyl) carbonate, and the like; di-(alkylphenyl)carbonates such as di-(tolyl)carbonate, and the like. Some other illustrative non-limiting examples of suitable diarylcarbonates include di-(naphthyl)carbonate, di-(chloronaphthyl)-carbonate, phenyl tolyl carbnate, chlorophenyl chloronaphthyl carbonate, and the like.

The preferred carbonate precursors are the carbonyl halides, with carbonyl chloride, also known as phosgene, being the preferred carbonyl halide.

One method which may be employed in preparing the polycarbonates of the instant invention involves the heterogeneous interfacial polymerization system utilizing an aqueous caustic solution, an organic water immiscible solvent, at least one dihydric phenol of Formula I, a catalyst, a carbonate precursor, and a molecular weight regulator. A preferred heterogeneous interfacial polymerization system is one which utilizes phosgene as the carbonate precursor.

Another useful method for preparing the carbonate polymers of the instant invention involves the use of an organic solvent system wherein the organic solvent system may also function as an acid acceptor, at least one dihydric phenol of Formula I, a molecular weight regulator, and a carbonate precursor. A preferred method is one wherein phosgene is utilized as the carbonate precursor.

Generally, in both of the aforedescribed methods phosgene is passed into a reaction mixture which contains at least one dihydric phenol of Formula I. The temperature at which the phosgenation reaction proceeds may vary from below 0° C. to above 100° C. The reaction proceeds satisfactorily at temperatures from room temperature (25° C.) to about 50° C. Since the reaction is exothermic, the rate of phosgene addition may be used to control the reaction temperature.

A suitable acid acceptor may be either organic or inorganic in nature. A suitable organic acid acceptor is a tertiary amine and includes such materials as pyridine, triethylamine, tributylamine, dimethylaniline, trimethylpyridine, etc. The inorganic acid acceptor may be a hydroxide, such as an alkali or alkaline earth metal hydroxide, a carbonate, a bicarbonate, a phosphate, and the like. An inorganic acid acceptor is preferred when an aqueous solvent system is used.

The catalysts which may be employed can be any of the well known catalysts which aid the polymerization reaction of the dihydric phenol with phosgene. Suitable catalysts include, but are not limited to, tertiary amines, secondary amines, quaternary ammonium compounds, quaternary phosphonium compounds, amidines, and the like.

The molecular weight regulators employed may be any of the known compounds which regulate the molecular weight of the carbonate polymers by a chain stopping or terminating mechanism. These compounds include, but are not limited to, phenol, tertiarybutyl phenol, and the like.

The amount of phosgene utilized is an amount effective to react with substantially all of the unreacted hydroxyl groups present on the nuclear aromatic residues of the dihydric phenols of Formula I. This amount is referred to as a stoichiometric amount.

The high molecular weight aromatic carbonate polymers of the instant invention generally have a weight average molecular weight in the range of from about 5,000 to about 200,000, preferably from about 10,000 to about 100,000, and more preferably from about 25,000 to about 50,000.

The polycarbonates of the instant invention will contain at least one repeating structural unit represented by the general formula

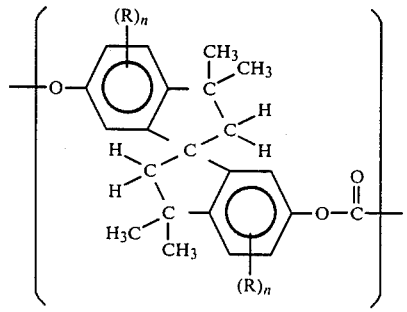

II.

wherein R and n are as defined hereinafore.

If only one dihydric phenol of Formula I is used than the polycarbonates will contain only one repeating structural unit of Formula II. If more than one dihydric phenol of Formula I is used the instant polycarbonates will contain more than one repeating structural unit of Formula II, the number and type of structural units being dependent on the number and type of dihydric phenols employed.

The polycarbonates of the instant invention may optionally have admixed therewith the commonly known and used additives such as, for example, antistatic agents; mold release agents; impact modifiers; inert fillers such as glass, talc, mica, and clay; ultraviolet radiation absorbers such as the benzophenones, benzotriazoles, and benzylidene malonates; hydrolytic stabilizers such as the epoxides disclosed in U.S. Pat. Nos. 3,489,716, 4,138,379 and 3,839,247, all of which are hereby incorporated herein by reference; color stabilizers such as the organophosphites disclosed in U.S. Pat. Nos. 3,305,520 and 4,118,370, both of which are incorporated herein by reference; and flame retardants.

Some particularly useful flame retardants include the alkali and alkaline earth metal salts of sulfonic acids. These types of flame retardants are disclosed in U.S. Pat. Nos. 3,933,734, 3,948,851, 3,926,908, 3,919,176, 3,909,490, 3,953,396, 3,931,100, 3,978,024, 3,953,399, 3,917,559, 3,951,910 and 3,940,366, all of which are incorporated herein by reference.

Another embodiment of the instant invention is a carbonate copolymer obtained by coreacting (i) a carbonate precursor, (ii) at least one spiro dihydric phenol of Formula I, and (iii) a conventional non-spiro dihydric phenol.

The non-spiro dihydric phenols are well known in the art and are disclosed, for example, in U.S. Pat. Nos. 3,028, 3,169,121, 3,275,601 and 4,111,910, all of which are incorporated herein by reference.

These non-spiro dihydric phenols will in general conform to the general formula

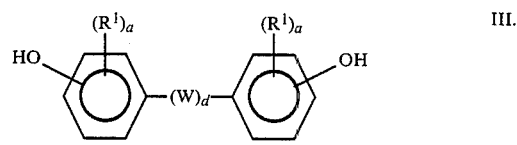

III.

wherein:
$R^1$ is independently selected from monovalent hydrocarbon radicals and halogen radicals;
a is independently selected from positive integers having a value of from 0 to 4 inclusive;
d is either zero or one; and
W is selected from divalent hydrocarbon radicals; —S—, —O—, —S—S—,

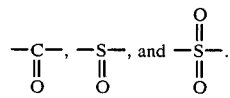

The monovalent hydrocarbon radicals represented by $R^1$ include the alkyl radicals, the cycloalkyl radicals, the aryl radicals, the aralkyl radicals, and the alkaryl radicals. The carbon atom limitations for each group are the same as for the aforementioned R group of Formula I. $R^1$ is preferably chloro, bromo, or alkyl of one to five carbon atoms, inclusive.

The divalent hydrocarbon radicals represented by W include the alkylene radicals of two to ten carbon atoms, the cycloalkylene radicals of four to seven carbon atoms, the alkylidene radicals of two to ten carbon atoms, and the cycloalkylidene radicals of four to seven carbon atoms. These divalent hydrocarbon radicals are the non-spiro radicals.

In the dihydric phenols represented by Formula III when more than one $R^1$ substituent is present they may be the same or different. Where d is zero in Formula III the aromatic rings are directly joined with no intervening alkylene or other bridge. The positions of the hydroxyl groups and $R^1$ on the aromatic nuclear residues can be varied in the ortho, meta, or para positions and the groupings can be in a vicinal, asymmetrical or symmetrical relationship where two or more ring carbon atoms of the aromatic hydrocarbon residues are substituted with R and hydroxyl group.

Some illustrative non-limiting examples of dihydric phenols of Formula III include:
2,2-bis(4-hydroxyphenyl)propane (bisphenol-A);
4,4'-dihydroxydiphenylmethane:
1,2-bis(4-hydroxyphenyl)ethane;
2,2-bis(3,5-dimethyl-4-hydroxyphenyl)propane;
1,1-bis(4-hydroxy-3-chlorophenyl)ethane:
2,2-bis(3,5-dichloro-4-hydroxyphenyl)propane;
4,4-thiodiphenol; and
1,1-bis(4-hydroxyphenyl)cyclohexane.

It is, of course, possible to employ a mixture of two or more different dihydric phenols of Formula III in preparing the copolycarbonates of the instant invention.

The copolycarbonates of this embodiment are prepared by coreacting (i) a carbonate precursor, (ii) at least on spiro dihydric phenol of Formula I, and (iii) at least one non-spiro dihydric phenol of Formula III in substantially the same manner and under substantially the same reaction conditions as described hereinafore.

The copolycarbonates of this embodiment will contain at least one repeating structural unit of Formula II and at least one repeating structural unit represented by the general formula

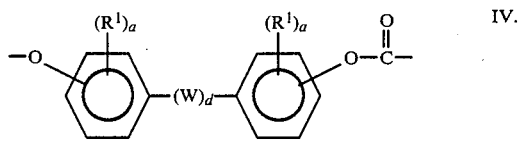

wherein $R^1$, W, a and d are as defined hereinafore.

The amount of the spiro dihydric phenol of Formula I employed in producing the copolycarbonates of this embodiment is an amount effective to improve the heat distortion temperatures of the copolycarbonates. That is to say, the copolycarbonates of this invention contain an amount of repeating structural units of Formula II effective to improve the heat distortion temperatures of the copolycarbonates. Generally, this amount is at least about 3 mole percent, based on the total amount of the repeating structural units of Formula II and Formula IV present. That is to say, the amount of the spiro dihydric phenol of Formula I employed in producing the instant copolycarbonates is at least about 3 mole percent, based on the total amounts of the spiro dihydric phenol of Formula I and the non-spiro dihydric phenol of Formula III used.

Generally, if the copolycarbonates of this embodiment contain less than about 3 mole percent of the repeating structural units of Formula II there will be no significant improvement in the heat distortion temperatures of the copolycarbonates, i.e., if less than about 3 mole percent of the spiro dihydric phenol of Formula I is used there will generally be no significant improvement in the heat distortion temperatures of the resultant copolycarbonates.

The upper limit of the amounts of the repeating structural units of Formula II present, i.e., the upper limit of the amount of the spiro dihydric phenol utilized, is not critical, but is instead governed by such secondary considerations as cost and the like. Generally, it is preferred to use no more than about 95 mole percent of the spiro dihydric pheol of Formula I, i.e., it is preferred that the copolcarbonates contain no more than about 95 mole percent of repeating structural units of Formula II.

Also included with the scope of this invention are the high molecular weight thermoplastic randomly branched polycarbonates. These randomly branched polycarbonates may be obtained by the incorporation of small amounts, prefereably between 0.05 and 2.0 mol percent (based on the quantity of the dihydric phenols used), of polyfunctional, i.e., trifunctional or greater, organic compounds, particularly compounds which have three or more phenolic hydroxyl groups. The polyfunctional organic compounds which may be used to form the randomly branched polycarbonates are disclosed in U.S. Pat. Nos. 3,635,895; 4,001,184; and 3,544,514, all of which are hereby incorporated herein by reference. These polyfunctional compounds are generally aromatic and contain at least three functional groups which may be carboxyl, hydroxyl, carboxylic anhydride, haloformyl, or mixtures thereof. Some illustrative non-limiting examples of these polyfunctional compounds include trimellitic anhydride, trimellitic acid, trimellityl trichloride, 4-chloroformyl phthalic anhydride, pyromellitic acid, pyromellitic dianhydride, mellitic acid, mellitic anhydride, trimesic acid, benzophenonetetracarboxylic acid, and the like.

Yet another embodiment of the instant invention is a polycarbonate blend comprised of (i) at least one carbonate polymer obtained by the reaction of at least one dihydric phenol of Formula I with a carbonate precursor, and (ii) at least one carbonate polymer obtained by the reaction of at least one dihydric phenol of Formula III with a carbonate precursor.

These polycarbonate blends are generally formed by first preforming the various carbonate polymers and thereafter physically mixing or blending the various carbonate polymers together.

The polycarbonate blends of this embodiment generally contain an amount of at least one carbonate polymer derived from the spiro dihydric phenol of Formula I effective to imrpove the heat distortion temperatures of the blends. Generally, this amount is at least about 3 weight percent, based on the total amounts of the polycarbonate derived from the spiro dihydric phenol of Formula 1 and the polycarbonate derived from the non-spiro dihydric phenol of Formula III present. In general, if these blends contain less than about 3 weight percent of the polycarbonate derived from the spiro dihydric phenol there will be no significant improvement in their heat distortion temperatures. The upper limit of the amount of the polycarbonate derived from the spiro dihydric phenol of Formula I is not critical but is controlled by such secondary considerations as cost and the like. Generally, it is preferred that these blends contain no more than about 95 weight percent of the poycarbonate derived from the spiro dihydric phenol of Formula I.

The instant blends may optionally have admixed therewith the aforedesribed commonly known and used additives.

Still another embodiment of the instant invention are the copolyester-carbonates of the spiro dihydric phenols of Formula I.

Briefly stated, the copolyester-carbonates of this embodiment comprise recurring carbonate groups

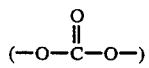

carboxylate groups

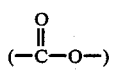

and aromatic carbocyclic groups in the polymer chain, in which at least some of the carboxylate groups and at least some of the carbonate groups are bonded directly to ring carbon atoms of the aromatic carbocyclic groups.

These copolyester-carbonates contain ester bonds and carbonate bonds in the polymer chain wherein the amount of ester bonds is in the range of from about 25 to about 90 mole percent, and preferably from about 35 to about 80 mole percent, based on the total amount of ester bonds and carbonate bonds present. For example, 5 moles of bisphenol-A reacting completely with 4 moles of isophthaloyl dichloride and 1 mole of phosgene would give a copolyester-carbonate containing 80 mole percent ester bonds.

The copolyester-carbonates of the instant invention are prepared by reacting (i) at least one spiro dihydric phenol of Formula I, (ii) at least one difunctional carboxylic acid or an ester forming reactive derivative tehreof, and (iii) a carbonate precursor.

In general, any difunctional carboxylic acid or its ester forming reactive derivative conventionally used in the preparation of linear polyesters may be utilized in the preparation of the copolyester-carbonate polymers of the instant invention. Generally, the carboxylic acids which may be used include the aliphatic carboxylic acids, the aromatic carboxylic acids, and the aliphatic-aromatic carboxylic acids. These acids are disclosed in U.S. Pat. No. 3,169,121, which is hereby incorporated herein by reference.

The difunctional carboxylic acids which may be used generally will conform to the general formula

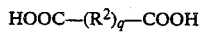     V.

wherein $R^2$ is an alkylene, alkylidene, cycloalkylene or cycloalkylidene group with carbon atom limitations for each $R^2$ the same as in W of Formula II; an aromatic group such as phenylene, biphenylene, substituted phenylene, substituted biphenylene, naphthylene, substituted naphthylene, and the like; two or more aromatic groups connected through non-aromatic linkages such as alkylene or alkylidene groups; and a divalent aralkyl radical such as tolylene, xylylene, and the like. The letter q represents either zero or one.

Preferred difunctional carboxylic acids are the aromatic dicarboxylic acids, i.e., those acids of Formula V wherein $R^2$ represents a divalent aromatic radical and q is one. The preferred aromatic dicarboxylic acids are those represented by the general formula

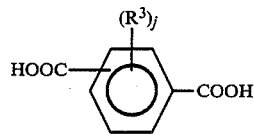

wherein:
$R^3$ is independently selected from monovalent hydrocarbon radicals and halogen radicals; and
j is a positive integer having a value of from 0 to 4 inclusive.

The monovalent hydrocarbon radicals represented by $R^3$ include the alkyl radicals, the cycloalkyl radicals, the aryl radicals, the aralkyl radicals, and the alkaryl radicals. The carbon atom limitations for each group are the same as for the aforementioned R group of Formula I.

The preferred halogen radicals are the chlorine and bromine radicals. Alkyl of one to five carbon atoms in also preferred.

Particularly useful aromatic dicarboxylic acids of Formula I are those wherein j is zero, and those wherein j is 1 to 3 and $R^3$ is an alkyl radical, preferably one containing from 1 to about 5 carbon atoms.

When more than one $R^3$ substituent is present on the ring carbon atoms of the aromatic carbocyclic residue they may be the same or different.

Mixtures of these carboxylic acids may be employed in lieu of individual carboxylic acid. Therefore, wherever the term difunctional carboxylic acid is employed herein it is meant to include mixtures of two or more different difunctional carboxylic acids as well as individual difunctional carboxylic acids.

Particularly useful aromatic dicarboxylic acids are isophthalic acid, terephthalic acid, and mixtures thereof.

Rather than utilizing the difunctional aromatic carboxylic acids per se it is possible, and sometimes even preferred, to employ the ester forming reactive derivatives of these acids. Illustrative of these ester forming reactive derivatives of these acids are the acid dihalides such as the acid dichlorides. Thus, for example, instead of using isophthalic acid, terephthalic acid, or mixtures thereof it is possible use isophthaloyl dichloride, terephthaloyl dichloride, or mixtures thereof.

The copolyester-carbonates of the instant invention will contain repeating structural units of Formula II and those represented by the general formula

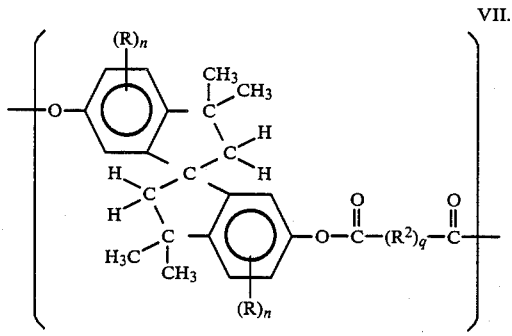

wherein R, $R^2$, n and q are as defined hereinafore.

The copolyester-carbonates of the instant invention may conveniently be prepared by the heterogeneous interfacial polymerization process. Such a process is disclosed, inter alia, in U.S. Pat. No. 3,169,121, which is hereby incorporated herein by reference.

The copolyester-carbonates of the instant invention may optionally contain admixed therewith the various additives described hereinafore.

Yet another embodiment of the instant invention is a copolyester-carbonate resin derived from the coreaction of (i) a carbonate precursor, (ii) at least one difunctional carboxylic acid or an ester forming reactive derivative thereof, (iii) at least one spiro dihydric phenol of Formula I, and (iv) at least one conventional non-spiro dihydric phenol of Formula III. In this embodiment the amount of the spiro dihydric phenol used to prepare these copolyester-carbonates is an amount effective to improve the heat distortion temperatures of the copolyester-carbonates. Generally this amount is at least about 3 mole percent, based on the total amounts of said spiro dihydric phenol and said conventional non-spiro dihydric phenol used. In general, if less than about 3 mole percent of said spiro dihydric phenol is used there is no significant imrpovement in the heat distortion temperatures of the copolyester-carbonates. The upper limit of the amount of said spiro dihydric phenol employed is not critical and is controlled by such secondary considerations as cost and the like. It is generally preferred that not more than about 95 mole percent of said spiro dihydric phenol be employed, based on the total amounts of the spiro dihydric phenol and the non-spiro dihydric phenol employed.

The copolyester-carbonates of this embodiment may optionally contain the aforedescribed additives.

Still another embodiment of the instant invention is a blend of spiro dihydric phenol based copolyester-carbonates and conventional non-spiro dihydric phenol based copolyester-carbonates. These blends exhibit improved heat distortion temperatures as compared to blends of conventional non-spiro dihydric phenol based copolyester-carbonates.

These blends are comprised of a physical mixture of (i) at least one copolyester-carbonate derived from (a) a carbonate precursor, (b) at least one difunctional carboxylic acid or an ester forming reactive derivative thereof, and (c) at least one spiro dihydric phenol of Formula I (hereinafter referred to as copolyester-carbonate resin A); and (ii) at least one copolyester-carbonate derived from (a) a carbonate precursor, (b) at least one difunctional carboxylic acid or an ester froming reactive derivative thereof, and (c) at least one conventional non-spiro dihydric phenol (hereinafter referred to as copolyester-carbonate resin B).

In this embodiment the copolyester-carbonate resins A and B are preformed and then physically mixed or blended together.

These blends contain an amount of copolyester-carbonate resin A effective to improve the heat distortion temperatures of the blends. Generally this amount is at least about 3 weight percent of resin A, based on the total amounts of resins A and B used. Generally if less than about 3 weight percent of resin A is used there will be no significant improvement in the heat distortion temperatures of the blends. The upper limit of the amount of resin A used is not critical but is generally governed by such secondary considerations as cost and the like. Generally it is preferred that the blends contain no more than about weight percent of the copolyester-carbonate resin A.

The instant blends may optionally have admixed therewith the aforedescribed commonly known and used additives.

DESCRIPTION OF THE PREFERRED EMBODIMENT

In order to more fully and clearly illustrate the present invention the following examples are set forth. It is intended that the examples be considered as illustrative rather than limiting the invention as disclosed and claimed herein. In the example all parts and percentages are on a weight basis unless otherwise indicated.

The following example illustrates polycarbonates falling outside the scope of the instant invention. This example is presented for comparative purposes only.

EXAMPLE 1

This example illustrates a conventional prior art polycarbonate derived from bisphenol-A and phosgene.

To a 2 liter reaction vessel there are added 34.2 grams (0.15 mole) of bisphenol-A, 0.03 gram (2.1 mole percent ) of phenol, 0.42 milliliter of triethylamine, 400 milliliters of methylene chloride and 300 milliliters of water. A 25% aqueous solution of sodium hydroxide is added to adjust the pH of the reaction mixture to 11 and thereafter to maintain it at pH 11. Into this reaction mixture are gradually introduced 18 grams of phosgene while maintaining the pH at about 11 by the introduction of said caustic solution. The methylene chloride layer is separated from the alkaline aqueous layer, washed with 0.01N aqueous hydrochloric acid, and is then washed twice with deionized water. The polycarbonate resin is precipitated with methanol and dried in a vacuum oven at 60° C.

The intrinsic viscosity of the resultant polycarbonate is found to be 0.574 dl/gm at 25° C. in methylene chloride.

In order to determine the heat distortion temperatures of the polycarbonate resin the glass transition temperature (Tg) of the resin is determined. As is well known to those skilled in the art the glass transition temperatures (Tg) can generally be used in place of the heat distortion temperatures since heat distortion temperatures are relatable to glass transition temperatures. Accordingly, glass transition temperatures have been measured to show resistance to high heat distortion of the polycarbonate resins of the present invention. The glass transition temperatures are determined by using a Perkin-Elmer DSC-2B instrument which measures the second order glass transition temperature or Tg by differential scanning calorimetry.

The results of this test are set forth in Table I.

The following examples illustrate the polycarbonates of the instant invention.

EXAMPLE 2

The procedure of Example 1 is substantially repeated except that the 34.2 grams of bisphenol-A are replaced with 17.1 grams of bisphenol-A and 23.1 grams of 3,3,3',3'-tetramethyl-1,1'-spirobiindane-6,6'-diol.

The Tg of the resultant polycarbonate is determined and the results are set forth in Table I.

EXAMPLE 3

The procedure of Example 1 is substantially repeated except that the 34.2 grams of bisphenol-A are replaced with 46.2 grams of 3,3,3',3'-tetramethyl-1,1'-spirobiindane-6,6'-diol.

The Tg of the resultant polycarbonate is determined and the results are set forth in Table I.

TABLE I

| Example No. | Tg (°C.) |
|---|---|
| 1 (Control) | 149.0 |
| 2 | 183.0 |
| 3 | 207.2 |

The following example illustrates a prior art conventional copolyester-carbonate. This example is presented for comparative purposes only.

EXAMPLE 4

This example illustrates a conventional prior art copolyester-carbonate derived from isophthaloyl dichloride, bisphenol-A, and phosgene.

To a 2 liter reaction vessel there are added 34.2 grams (0.15 mole) of bisphenol-A, 0.30 gram (2.1 mole %) of phenol, 0.42 milliliter of triethylamine, 400 milliliters of methylene chloride and 300 milliliters of water. A 25% aqueous solution of sodium hydroxide is added to adjust the pH of the reaction mixture to about 11 and thereafter to maintain it at a pH of about 11. Isophthaloyl dichloride, 15.2 grams (0.075 mole), dissolved in 20 grams of methylene chloride is added dropwise to the reaction mixture over a period of 5 minutes while maintaining the pH at about 11 with the use of an automatic titrator. After the pH becomes stable, without the use of additional caustic solution, phosgene is introduced into the reaction mixture at the rate of 0.5 gram per minute for 26 minutes while maintaining the pH at about 11 by the addition of the aqueous caustic solution. The amount of phosgene added is 13 grams (0.133 mole). The methylene chloride layer is separated from the alkaline aqueous layer, washed with 0.01N aqueous hydrochloric acid, and is then washed twice with deionized water. The copolyester-carbonate resin is precipitated with methanol and dried in a vacuum oven at 60° C.

The Tg of this copolyester-carbonate is determined and the results are set forth in Table II.

The following example illustrates a copolyester-carbonate of the instant invention.

EXAMPLE 5

This example illustrates the preparation of a copolyester-carbonate from isophthaloyl dichloride, phosgene and a spiro dihydric phenol.

To a reactor vessel there are added 400 milliliters of methylene chloride, 300 milliliters of water, 7.7 grams of 3,3,3',3'-tetramethyl-1,1'-spirobiindane-6,6'-diol, 5.7 grams of bisphenol-A, 0.07 gram of phenol, and 0.4 milliliter of triethyamine. At a pH of 11, achieved by the addition of a 25% aqueous solution of sodium hydroxide, 2.0 grams of isophthaloyl dichloride dissolved in methylene chloride are added dropwise over a 15 minute period, while maintaining the pH at about 11 by the addition of the caustic solution. After addition of the isophthaloyl dichloride is completed 5 grams of phosgene are introduced over a 15 minute period while maintaining the pH at about 11 by the use of the aqueous caustic solution. The polymer mixture is diluted with methylene chloride and the brine phase is separated. The resulting polymer containing phase is washed with 0.01N aqueous hydrochloric acid followed by two water washings. The polymer is then precipitated with methanol.

The Tg of this copolyester-carbonate is determined and the results are set forth in Table II.

TABLE II

| Example No. | Tg (°C.) |
|---|---|
| 4 (Control) | 170.6 |
| 5 | 201.0 |

As illustrated by the data in Table I the polycarbonates of the instant invention, i.e., Examples 2 and 3, exhibit significantly higher glass transition temperatures than the prior art conventional polycarbonates, i.e., Example 1. The polycarbonate of Example 2, which is derived from 50 mole percent of the spiro dihydric phenol and 50 mole percent of bisphenol-A, exhibits a Tg which is 34 degrees C. higher than the prior art conventional polycarbonate of Example 1 which is derived solely from bisphenol-A.

The data of Table II also illustrate that the instant copolyester-carbonates, i.e., Example 5, exhibit significantly higher glass transition temperatures than the conventional prior art copolyester-carbonates, i.e., Example 4.

The instant polycarbonates and copolyester-carbonates may be used to produce high heat resistant films and molded articles.

Other modifications and variations of the present invention are possible in light of the above disclosure. It is, therefore, to be understood that changes may be made in the particular embodiments described above which are in the full intended scope of the invention as defined in the appended claims.

What is claimed is:

1. Aromatic thermoplastic polymer exhibiting improved heat distortion temperatures derived from:
   (i) a carbonate precursor; and
   (ii) at least one spiro dihydric phenol selected from spiro dihydric phenols represented by the general formula

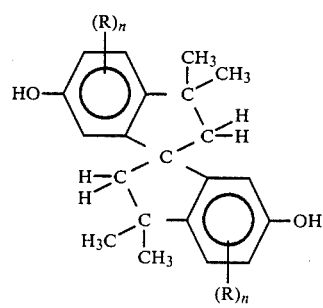

wherein:
R is independently selected from monovalent hydrocarbon radicals or halogen radicals; and
n is independently selected from positive integers having a value of from 0 to 3 inclusive.

2. The polymer of claim 1 wherein said halogen radicals are selected from bromine or chlorine radicals.

3. The polymer of claim 1 wherein said monovalent hydrocarbon radicals are selected from alkyl radicals, cycloalkyl radicals, aryl radicals, aralkyl radicals, or alkaryl radicals.

4. The polymer of claim 3 wherein said monovalent hydrocarbon radicals are selected from alkyl radicals.

5. The polymer of claim 1 wherein n is zero.

6. The polymer of claim 1 wherein said carbonate precursor is phosgene.

7. The polymer of claim 6 wherein said spiro dihydric phenol is 3,3,3'3'-tetramethyl-,1,1'-spirobiindane-6,6'-diol.

8. The polymer of claim 1 which are derived from (i); (ii); and
(iii) at least one dihydric phenol represented by the general formula

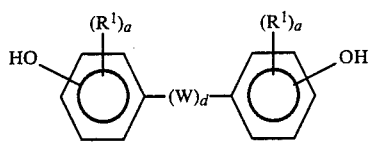

wherein:
$R^1$ is independently selected from monovalent hydrocarbon radicals or halogen radicals;
a is independently selected from positive integers having a value of from 0 to 4 inclusive;
d is either zero or one; and
W is selected from non-spiro divalent hydrocarbon radicals, —S—, —O—, —S—S—,

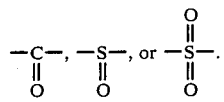

9. The polymer of claim 8 wherein the amount of the spiro dihydric phenol of (ii) employed is an amount effective to improve the heat distortion temperatures of said polymers.

10. The polymer of claim 9 wherein said amount is at least about 3 mole percent, based on the total amounts of said spiro dihydric phenol of (ii) and said non-spiro dihydric phenol of (iii) used.

11. The polymer of claim 9 wherein said divalent hydrocarbon radicals represented by W are selected from alkylene radicals, cycloalkylene radicals, alkylidene radicals, or cycloalkylidene radicals.

12. The polymer of claim 11 wherein said monovalent hydrocarbon radicals represented by $R^1$ are selected from alkyl radicals, cycloalkyl radicals, aryl radicals, aralkyl radicals, or alkaryl radicals.

13. The polymer of claim 9 wherein the non-spiro dihydric phenol of (iii) is bisphenol-A.

14. The polymer of claim 13 wherein said carbonate precursor is phosgene.

15. The polymer of claim 14 wherein said spiro dihydric phenol of (ii) is 3,3,3'3'-tetramethyl-1,1'-spirobiindane-6,6'-diol.

* * * * *